US007097451B2

(12) United States Patent
Tang

(10) Patent No.: US 7,097,451 B2
(45) Date of Patent: Aug. 29, 2006

(54) THERMOPLASTIC SURGICAL TEMPLATE FOR PERFORMING DENTAL IMPLANT OSTEOTOMIES AND METHOD THEREOF

(76) Inventor: Brian Tang, 1328 W. El Camino Real, Suite #1, Mountain View, CA (US) 94040

( * ) Notice: Subject to any disclaimer, the term of this patent is extended or adjusted under 35 U.S.C. 154(b) by 0 days.

(21) Appl. No.: 10/917,202

(22) Filed: Aug. 11, 2004

(65) Prior Publication Data

US 2005/0106531 A1 May 19, 2005

Related U.S. Application Data

(60) Provisional application No. 60/556,596, filed on Mar. 26, 2004, provisional application No. 60/520,423, filed on Nov. 14, 2003.

(51) Int. Cl.
*A61C 3/02* (2006.01)

(52) U.S. Cl. .......................................... 433/76; 606/96

(58) Field of Classification Search .................. 433/72, 433/74, 75, 76; 606/96
See application file for complete search history.

(56) References Cited

U.S. PATENT DOCUMENTS 3,407,503 A 10/1968 Nealon
3,445,935 A 5/1969 Marshall
4,998,881 A 3/1991 Lauks
5,015,183 A 5/1991 Fenick
5,133,660 A 7/1992 Fenick
5,154,548 A * 10/1992 Walsh ...................... 408/72 R
5,213,498 A * 5/1993 Pelerin ........................ 433/37
5,320,529 A 6/1994 Pompa
5,388,933 A 2/1995 Dunbar
5,415,546 A 5/1995 Cox, Sr.
5,431,563 A * 7/1995 Huybrechts, Robert ...... 433/48
5,484,285 A 1/1996 Morgan et al.
5,556,278 A 9/1996 Meitner
5,575,656 A 11/1996 Hajjar
5,613,852 A 3/1997 Bavitz
5,636,986 A 6/1997 Pezeshkian
5,718,579 A 2/1998 Kennedy
5,725,376 A 3/1998 Poirier
5,733,077 A * 3/1998 MacIntosh, Jr. ............ 408/103
5,741,133 A 4/1998 Gordils et al.
5,775,900 A 7/1998 Ginsburg et al.

(Continued)

FOREIGN PATENT DOCUMENTS

GB 2401053 * 11/2004

OTHER PUBLICATIONS

Higginbottom, Frank. Oct. 2003, *Fabrication of a Radiographic Guide and Surgical Template*, Step-by-Step Instructions by Institut Straumann, Switzerland.

(Continued)

*Primary Examiner*—Ralph A. Lewis
(74) *Attorney, Agent, or Firm*—David Pressman

(57) ABSTRACT

A surgical template for performing dental implant osteotomies comprises a malleable, resinous, thermoplastic base, at least one non-thermoplastic, rigid drill guide attached to the base, and a securing mechanism between the base and the drill guide. The template may reversibly melt to a malleable state and can be handled by hand without additional tools so as to conform to the adjacent teeth of the edentulous ridge, either directly in the patient's mouth or on a cast model. Dental osteotomies using the template can then be performed. The surgical template may be manufactured of a thermoplastic material having a sharp and low melting point but high rigidity in the solid state at room temperature.

40 Claims, 10 Drawing Sheets

20
22
23
12
10

U.S. PATENT DOCUMENTS

| | | | |
|---|---|---|---|
| 5,800,168 | A | 9/1998 | Cascione et al. |
| 5,888,065 | A | 3/1999 | Sussman |
| 5,915,962 | A | 6/1999 | Rosenlicht |
| 5,954,769 | A | 9/1999 | Rosenlicht |
| 5,967,777 | A | 10/1999 | Klein et al. |
| 5,989,025 | A | 11/1999 | Conley |
| 6,062,856 | A | 5/2000 | Sussman |
| 6,290,497 | B1 | 9/2001 | Di Emidio |
| 6,296,483 | B1 | 10/2001 | Champleboux |
| 6,319,006 | B1 | 11/2001 | Scherer et al. |
| 6,332,775 | B1 | 12/2001 | Gordils Wallis |
| 6,464,924 | B1 * | 10/2002 | Thornton ............... 264/331.12 |
| 6,592,368 | B1 | 7/2003 | Weathers, Jr. |
| 6,626,667 | B1 | 9/2003 | Sussman |
| 6,634,883 | B1 | 10/2003 | Ranalli |
| 6,672,870 | B1 | 1/2004 | Knapp |
| 2002/0177104 | A1 | 11/2002 | Klein et al. |
| 2003/0165791 | A1 | 9/2003 | Carmichael et al. |

OTHER PUBLICATIONS

The Dow Chemical Company, *TONE Polymers Products, Performance, Applications*, Mar. 2002, pp. 1-16.

* cited by examiner

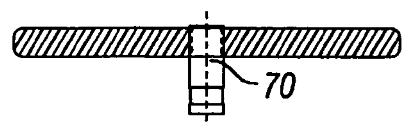
FIG. 9
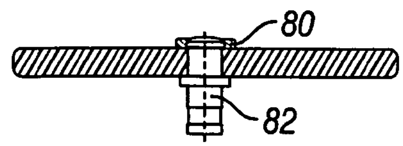
FIG. 10
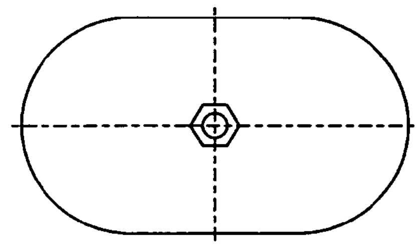
FIG. 9A
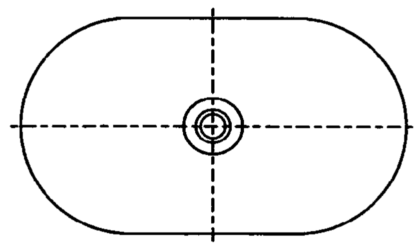
FIG. 10A
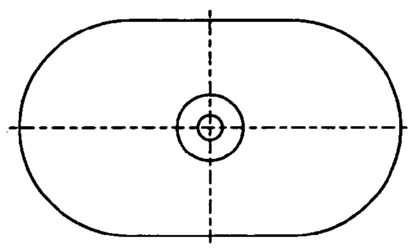
FIG. 11
FIG. 11A

THERMOPLASTIC SURGICAL TEMPLATE FOR PERFORMING DENTAL IMPLANT OSTEOTOMIES AND METHOD THEREOF

CROSS-REFERENCE TO RELATED APPLICATIONS

This application claims priority of U.S. Provisional Applications Nos. 60/520,423, filed Nov. 14, 2003, and 60/556,596, filed Mar. 26, 2004, which are incorporated herein by reference.

BACKGROUND OF THE INVENTION

1. Field of Invention

The present invention generally relates to dentistry, specifically to a method of making and using a surgical template for performing one or more dental implant osteotomies that can be molded directly in a patient's mouth or on a cast model.

2. Prior Art

In contemporary dental surgery, a prosthetic tooth is often used to replace a missing tooth. Typically, the prosthetic tooth is mounted on a dental implant that is secured in the jawbone of the recipient. The dental implant must be securely mounted in sufficient bone tissue so that it is as stable as a natural tooth root.

The conventional procedure for installing a dental implant includes performing an osteotomy, or drilling a hole in the maxillary (upper) or mandibular (lower) jawbone of the patient, inserting the implant in the hole, and attaching a prosthetic tooth to the implant. The dental implant is generally made of titanium or a high titanium alloy that can readily integrate with the recipient's jawbone.

The hole formed by the osteotomy must be located at a precise distance from adjacent teeth in order to guarantee a proper fit and cosmetic result for the prosthetic device. The hole must also be accurately located so that the implant is sufficiently anchored in the bone structure of the patient's jaw without causing injury to any vital structure, such as a nerve bundle.

Many techniques for locating the implant hole have been used in the past. It is known in dental surgery to make a cast model of the patient's mandible and/or maxilla in order to design or select the appropriate prosthetic device. Moreover, it is known to use a diagnostic tooth setup on the cast model to determine the most desirable tooth position in the final restoration. In locating and creating the hole for a dental implant, however, the most commonly used method is to survey the edentulous area (missing tooth space) visually and drill according to visual inspection. This free-handed technique is clearly not very precise because of the limited access and visibility in the patient's mouth, especially in the posterior region.

Other techniques for performing an osteotomy are available. U.S. Pat. No. 5,015,183 to Fenick (May 14, 1991) describes a method involving a casting having a radiopaque marker which is inserted in the patient's mouth. A series of x-rays are then taken to establish a trajectory for the proposed hole in the patient's jawbone. While the method provides an accurate means to locate the implant hole, it requires multiple x-rays, subjecting the patient to undesirable exposure levels, and is expensive and time-consuming.

U.S. Pat. No. 5,556,278 to Meitner (Sep. 17, 1996) describes a method and apparatus for locating an implant hole that has been commonly used by dental professionals for many years. This method involves creating a cast model of the patient's jaw and then placing a diagnostic tooth setup made from wax or other material in the edentulous space. A hole is then drilled through the diagnostic tooth setup into the jaw model. This hole corresponds to the prospective osteotomy in the patient's real dental arch and therefore the location and orientation of the hole will correspond to an optimum location and orientation of the implant osteotomy. A guide post, whose design and dimension can vary, is then inserted into the hole with a portion of it projecting from the base of the edentulous ridge. A guide sleeve is then slid over the projecting part of this guide post until the base end of the sleeve rests in contact with the cast arch.

A non-bonding, separating medium, such as wax, is then applied on the cast arch in the edentulous space and on the cast tooth surfaces wherever the template forming material will be applied. This procedure is used to facilitate the removal of the template from the cast model once the resin is cured, since most resins have a high degree of polymerization shrinkage when set. A template material, preferably a self-cured or light-cured resin material, is then applied to the cast arch around the sleeve in the edentulous space and around at least one tooth adjacent to each side of the edentulous space. Once the resin has completely cured, the template is trimmed to an appropriate size. It is then inserted into the patient's mouth and the position and orientation of the guide sleeve can be radiographically visualized before the hole is drilled.

Dr. Frank Higginbottom describes an alternative but similar method of fabricating a surgical template, in Higginbottom, Frank, 2003 October, *Fabrication of a Radiographic Guide and Surgical Template*, Step-by-Step Instructions by Institut Straumann, Switzerland. In this procedure, a guide post is also secured-into the patient's cast model first. However, instead of applying a self- or light-cured resin, a thick resin sheet is placed onto the entire cast model and vacuum-formed under high-powered suction from a vacuum former combined with high heat, usually in excess of 149° C. (300° F.). Excess material below the height of the contour of the adjacent teeth is then trimmed away. A significant amount of time is required to trim away the excess material because the resin sheet is vacuum-formed over the entire model. Further, unless all the undercuts of the model have been adequately blocked out by a separating medium, the model is frequently damaged or destroyed during the removal of this resin layer due to the thermal shrinkage of the resin material.

While the Meitner and Higginbottom methods provide relatively accurate means to locate an implant hole, their templates are complicated to fabricate and cannot be directly made in a patient's mouth. The setting and hardening process of the resin usually involves a physical and/or chemical change that is not reversible, and in the event of a mistake, the whole resin application step must be repeated. Further, in practice these procedures are very time consuming due to the multiple steps, equipment, and materials involved in fabricating the template. Particularly, the process of applying the separating medium and the resin (self-cured, light-cured, or vacuum-formed), and the removal, trimming, and polishing of the hardened resin usually takes significant amounts of time even with a trained hand.

U.S. Pat. No. 5,989,025 to Conley (Nov. 23, 1999) describes a drill guide apparatus for use in preparing a dental implant site comprising a tubular drill guide with an external screw thread, a stent with an external screw thread, and an attachment part that removably attaches to the drill guide. The screw threads enable the tubular drill guide to be removably engaged with the stent. The attachment part also has screw threads which are complementary to the screw threads of the tubular drill guide and can function as a radiographic marker or for other purposes. The problem with this approach is that there are a number of small removable parts and attachments that a patient may accidentally swallow or inhale during surgery. Further, it is difficult for the surgeon to manipulate various removable attachments while performing the intended osteotomy.

U.S. Pat. No. 5,775,900 to Ginsburg et al. (Jul. 7, 1998) describes a thermally deformable clear acrylic resin removable prosthetic stent which is configured to form a full or partial removable prosthesis. The stent becomes moldable when heated to above 49° C. (120° F.) for a few minutes. The stent may then be formed on a model of the patient's teeth or intraorally. Once formed and chilled, the stent becomes stable and can be used as a surgical and radiographic stent. However, this stent comprises only a clear acrylic resin and does not enable the use of any drill guide which is critical for providing an accurate means to locate an implant hole and to guide the drill in the right direction when performing the intended osteotomy. Further, the operator must first perform the extra steps of mixing a plasticized methyl methacrylate liquid monomer with a methyl methacrylate polymer powder, and then curing the mixture at high pressure (68.9–137.9 bar or 1000–2000 psi) and high temperature (145° C.–155° C.) for four to eight minutes in order to produce the moldable acrylic resin.

Others have recently described surgical templates that are fabricated using advanced computer technologies. For example, U.S. Pat. No. 5,967,777 to Klein et al. (Oct. 19, 1999) describes a surgical template assembly having one or more drill guides and one or more dental implant guides which are precisely located via a computer-driven milling machine. The method involved comprises the steps of fitting a CT (computerized tomography) scan appliance to a patient's mouth, obtaining CT scan data of the patient's jawbone and the CT scan appliance, and computer generating an image of the patient's jawbone from the CT scan data and a simulation of a dental implant. This method requires the operator to possess specialized computer and technological skills beyond those of an average dental professional, and is both very expensive and time-consuming.

While some of the above discussed methods will locate the implant hole with good accuracy, their templates are complicated and time-consuming to fabricate, and usually require numerous steps, equipment, and materials. The newer advanced computer technologies used in making the template also require the operator to possess specialized training and skills. Alternatively, many dental surgeons in the past have opted to go to dental laboratories to fabricate the template according to the older methods, rather than do it themselves. However, these laboratories charge a relatively high fee to fabricate the template and ultimately result in a longer wait for the patient to finally receive a customized template for the osteotomy.

Thus existing surgical templates for performing dental implant osteotomies are not user-friendly. These templates are complicated, require many steps, equipment, and materials to fabricate. These templates are also not easy to operate.

Objects and Advantages

It is accordingly a principal object of one aspect of the invention to provide an improved method of fabricating a template and an improved template for performing dental implant osteotomies. Further objects are to provide such a template which allows an operator to quickly fabricate a surgical template manually, either directly in a patient's mouth or on a cast model in minutes using hot water alone, without going through the numerous and tedious steps in making a traditional vacuum-formed or cured resin template, or spending a significant amount of money for a commercial laboratory to fabricate the device.

Yet further objects of other aspects of the invention are to provide a surgical template consisting of at least one rigid drill guide that provide an accurate means to locate the implant hole and to guide the drill in the correct orientation when performing the intended osteotomies; to provide a surgical template for performing osteotomies having at least one drill guide securely locked in a thermoplastic base, thus creating a strong one-piece device to prevent a patient from accidentally swallowing or inhaling loose parts or attachments during surgery; to provide a surgical template with a thermoplastic base that can reversibly soften in heated water into a malleable material that can be remolded and adjusted by hand without additional tools so that should a mistake occur, the operator can make corrective adjustments easily; to provide a surgical template with a variety of pre-molded base sizes to provide the best custom fit for the intended patient and further to minimize trimming of excess base material and to provide better visibility during surgery; and to provide a surgical template that requires no advance technical or computer knowledge from the operator so that any person skilled in the art of dental surgery can quickly learn to fabricate and operate this device.

Still further objects of other aspects of the invention will become apparent from a consideration of the ensuing description and drawings.

SUMMARY OF THE INVENTION

According to the present invention, one or more dental implant osteotomies are performed by providing a template having a base and a drill guide; softening its base in hot water until the base is malleable; manually manipulating the base while malleable to conform closely to the teeth next to the edentulous ridge, either directly in the patient's mouth or on a cast model; adjusting the drill guide to a desired position and axis corresponding to a prospective osteotomy; allowing the template to cool until the base is hardened; verifying the template is stable and retentive in the patient's mouth and the drill guide is angled correctly in all directions; and drilling a hole in the jawbone with a drill bit, using the stable custom-molded surgical template as a guide.

The template comprises a malleable, resinous, thermoplastic base, at least one non-thermoplastic, rigid drill guide fixed in the base, and a locking mechanism between the base and the drill guide. The base of the template comprises a material having a low and sharp melting point but high rigidity in the solid state. This material will reversibly soften to a malleable state upon heating in hot water, typically between the temperature range of 40–100° C., and remain moldable by hand to conform to surfaces of the teeth adjacent to the edentulous ridge before reaching room temperature. While the base is still soft the rigid drill guide can be oriented in the ideal position and axis corresponding to the prospective osteotomy. As the template cools, the base hardens into a hard and retentive matrix with a drill guide firmly incorporated within; thus providing the dental surgeon a stable surgical guide during dental implant osteotomy.

The template can also include various shapes to allow better visibility during surgery and various sizes to accommodate different patients.

Various locking mechanisms can be provided between the thermoplastic base and drill guide to create a strong and stable one-piece device.

Drill guides can have varying inner diameters that are color-coded for easy identification.

BRIEF DESCRIPTION OF THE DRAWINGS

Figures

FIG. 9 shows a sectional view and FIG. 9A shows a top view of the template illustrating a tap-locking-by-screw mechanism between the base and the drill guide.

FIG. 10 shows a sectional view and FIG. 10A shows a top view of the template illustrating a locking-by-two-parts-closed-fit mechanism between the base and the drill guide.

FIG. 11 shows a sectional view and FIG. 1A shows a top view of the template illustrating a locking-by-click-lock mechanism between the base and the drill guide.

Figure 1:
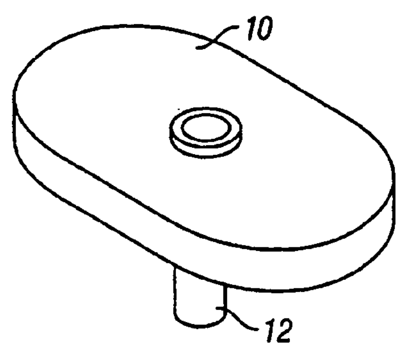
FIG. 1 shows a basic structure of a thermoplastic surgical template for performing a dental osteotomy according to the invention.

| Reference Numerals | | | |
|---|---|---|---|
| 10 | thermoplastic base | 12 | drill guide |
| 12A | inner diameter of drill guide | 12B | length of drill guide |
| 14 | color-coding on drill guide | 16 | locking mechanism |
| 18 | cast model | 20 | patient's mouth |
| 22 | surgical drill | 23 | custom-molded surgical template |
| 24 | edentulous area | | |
| 32 | nut | 30 | head bolt |
| 40 | rod | 34 | threads |
| 60 | fastener | 50 | knurling |
| 80 | headpiece | 70 | screw |
| 90 | click lock | 82 | body |

DETAILED DESCRIPTION

FIG. 1—Template

One embodiment of a dental template for accurately performing osteotomies according to the invention includes a thermoplastic pre-molded surgical template as shown in the isometric view of FIG. 1. The template has a thermoplastic base 10 that will soften in hot water to a malleable state Base 10 has the physical properties of a low and sharp melting point (typically within the temperature range of 40° C.–100° C.) but having high rigidity at the solid state in room temperature. Base 10 can vary in dimension, shape, color and composition to allow better visibility during surgery and best custom fit between patients. An exemplary shape for base 10 is an elongated ellipse, as shown in FIG. 1, that is about 40×20×2 mm in size.

An exemplary material for base 10 is a polymer sold under the trademark TONE P-787 by Dow Chemical Company, U.S.A. TONE polymers are homopolymers of $\epsilon$-caprolactone which exhibit a low and sharp melting point (60° C.), have excellent melt formability with low surface tackiness so as to be easily molded by hand, and high rigidity in the solid state at room temperature. TONE polymers have traditionally been used as a plaster replacement in orthopedic or orthotic application for the immobilization of body areas because of their unique properties. Other thermoplastic material of similar physical properties (i.e., a sharp and low melting point within the range of 40–100° C., and high rigidity in the solid state) can also be used in fabricating an embodiment of the template.

This embodiment of the template also includes a tubular drill guide 12 fixed in base 10 as shown in FIG. 1. Drill guide 12 can be made of a variety of non-thermoplastic, rigid materials, such as metals, plastics, composites, or ceramics. If drill guide 12 is made of a radiopaque material (such as stainless steel), it can further be used as a radiographic marker for evaluating the positioning, vertical height of bone and tissue, and magnification rate, thus eliminating the need to fabricate a separate radiographic template. An exemplary shape for drill guide 12 is a hollow cylindrical tube, as shown in FIG. 1, having an exemplary length 12B of about 10 mm with an inner diameter 12A of about 2 mm.

FIG. 2—Side View

Figure 2:
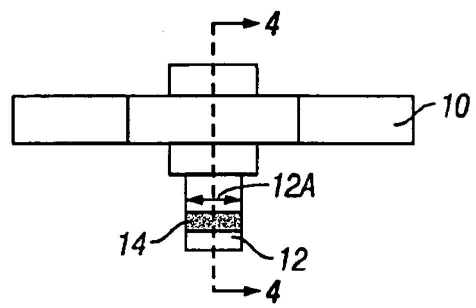
FIG. 2 shows a side view of the template illustrating a color-coded drill guide.

FIG. 2 shows a side view of the template of FIG. 1. Fixed in base 10 is rigid drill guide 12 which can have various inner diameters 12A and lengths 12B. The diameter and length of guide 12 can be selected to accommodate the many drill lengths and sizes of different dental implant systems in the market. Color-coding 14 may be applied to drill guide 12 corresponding to its inner diameter 12A for easy identification. For example, a drill guide 12 with an inner diameter 12A of 2.30 mm, corresponding to a standard dental implant pilot drill, is colored red, while one with an inner diameter 12A of 2.80 mm is colored blue. Other identification markers may also be placed on drill guide 12, such as etchings, imprints, or other non-colored markings.

FIG. 3—Top View

Figure 3:
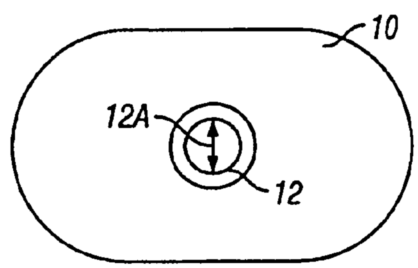
FIG. 3 shows a top view of the template.

A top view of the preferred embodiment of the template is shown in FIG. 3. As mentioned above, inner diameter 12A of drill guide 12 fixed in base 10 can vary to accommodate the different drill sizes of the various dental implant systems in the market. For example, the pilot drill for one dental implant system sold under the trademark Straumann of Institut Straumann, Switzerland is 2.2 mm in diameter, while the pilot drill for another system sold under the trademark IMTEC Sendax MDI (Mini Dental Implant) by IMTEC Corporation, U.S.A. is only 1.1 mm in diameter. Each of these systems therefore needs a drill guide 12 of a different inner diameter 12A to guide its respective drill.

Figure 4:
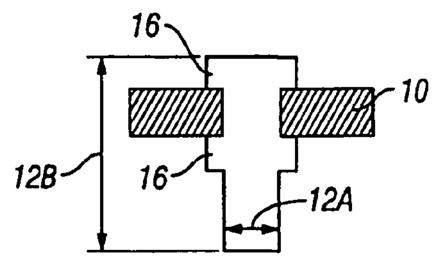
FIG. 4 shows a sectional view of the template illustrating a locking mechanism between a base and a drill guide of the template.

FIG. 4—Sectional View

FIG. 4 shows a sectional view of this embodiment of the template including a locking mechanism 16 between base 10 and drill guide 12 to create a strong and stable one-piece device. Locking mechanism 16 comprises enlarged portions of drill guide 12 resting above and below base 10 such that drill guide 12 is securely locked in base 10.

FIGS. 5–11—Other Embodiments

Figure 5:
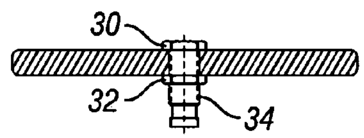
FIG. 5 shows a sectional view and FIG. 5A shows a top view of the template illustrating a locking-by-bolt-and-nut mechanism between the base and the drill guide.
Figure 6:
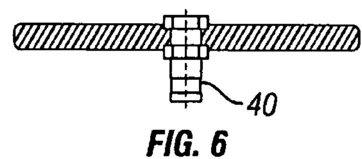
FIG. 6 shows a sectional view and FIG. 6A shows a top view of the template illustrating a locking-by-insert molding with an inlay mechanism between the base and the drill guide.
Figure 7:
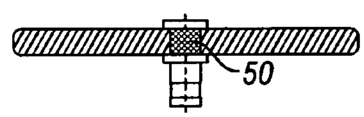
FIG. 7 shows a sectional view and FIG. 7A shows a top view of the template illustrating a locking-by-insert molding with an inlay (surface knurling) mechanism between the base and the drill guide.
Figure 8:
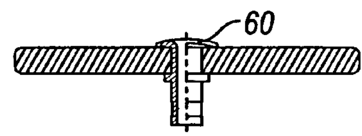
FIG. 8 shows a sectional view and FIG. 8A shows a top view of the template illustrating a locking-by-fastener mechanism between the base and the drill guide.

Further embodiments of the template include various locking mechanisms that may be employed to secure base 10 to drill guide 12 as shown in FIGS. 5–11. Such locking mechanisms include but are not limited to locking by bolt-and-nut, as shown in FIG. 5; locking by insert molding with an inlay, as shown in FIG. 6; locking by insert molding with an inlay (surface knurling), as shown in FIG. 7; locking by a fastener, as shown in FIG. 8; tap locking by a screw, as shown in FIG. 9; locking by two parts with a closed fit, as shown in FIG. 10; and locking by a click lock, as shown in FIG. 11.

Regardless of the locking mechanism used to secure base 10 to drill guide 12, the template is a one-piece device that is not meant to be disassembled, and has no removable screw thread or attachment parts. The manipulation of the template at time of use does not involve assembling any pieces and it is a single body at all times, whether softened, molded, or hardened for use.

Figure 5A:
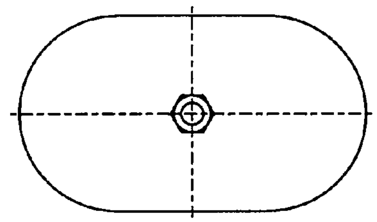

FIGS. 5 and 5A—Sectional View and Top View—Bolt-and-Nut

The locking by bolt-and-nut mechanism of FIGS. 5 and 5A comprises a head bolt 30 which can have various shapes, such as hexagonal, round, or square and is secured by a suitable nut 32. The head bolt and nut are made of metal, plastic, or a composite and can have right or left hand threads 34.

Figure 6A:
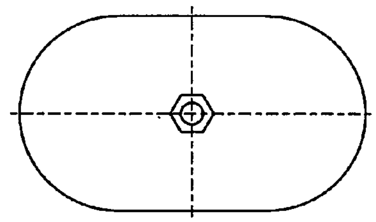

FIGS. 6 and 6A—Sectional View and Top View—Insert Molding with Inlay

The alternative embodiment illustrated in FIGS. 6 and 6A comprises a rod 40 having any variety of bolt head shapes. Rod 40 is made of metal, plastic, or a composite.

Figure 7A:
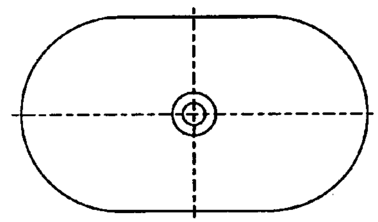

FIGS. 7 and 7A—Sectional View and Top View—Surface Knurling

In the embodiment of FIGS. 7 and 7A, the mechanism comprises a rod having any variety of bolt head shapes. The rod is made of metal, plastic or a composite and the inlay surface of the rod has diamond or straight knurling 50.

Figure 8A:
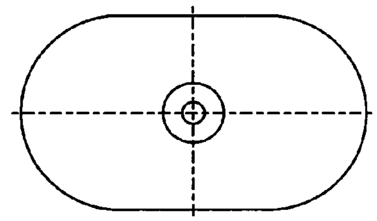

FIGS. 8 and 8A—Sectional View and Top View—Fastener

In the embodiment of FIGS. 8 and 8A, a fastener 60 which is bent at the head in order to insert drill guide 12 into a hole in base 10. Fastener 60 is made of metal.

FIGS. 9 and 9A—Sectional View and Top View—Screw

In FIGS. 9 and 9A, the tap-locking-by-screw mechanism comprises a metal or plastic screw 70 for screwing drill guide 12 into base 10.

FIGS. 10 and 10A—Sectional View and Top View—Closed Fit

FIGS. 10 and 10A show an embodiment in which the two parts are locked by a closed-fit mechanism comprising a metal or plastic body 82 for securing to the underside of base 10. Body 82 is attached to a head piece 80 to prevent the parts from disassembling.

FIGS. 11 and 11A—Sectional View and Top View—Click Lock

In FIGS. 11 and 11A, the locking-by-click-lock mechanism comprises a push-in and click lock mechanism 90 for securing drill guide 12 into base 10.

Figure 12:
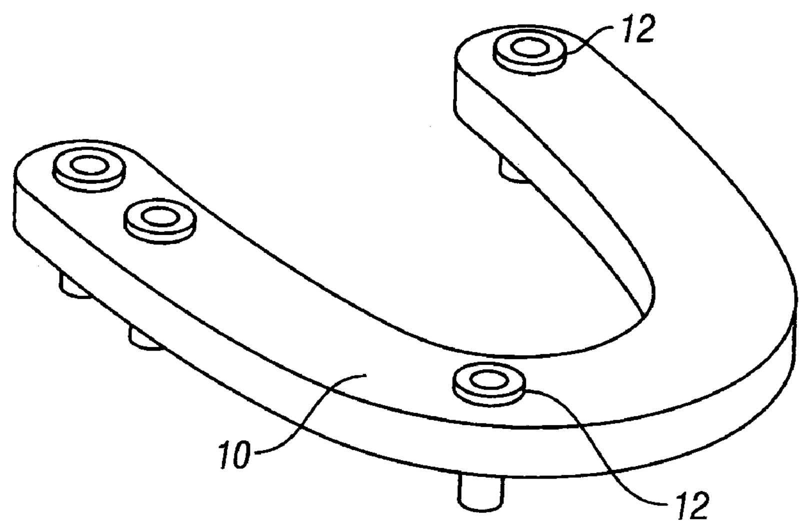
FIG. 12 shows a template with more than one fixated drill guide for multiple dental implant osteotomies.
Figure 13:
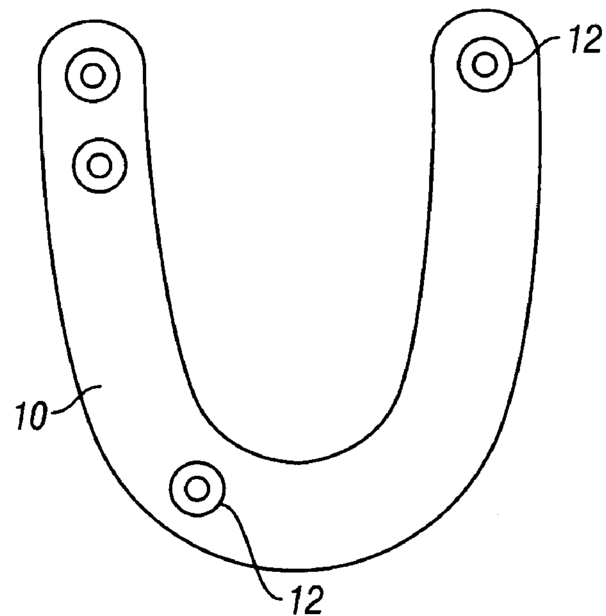
FIG. 13 shows a top view of the surgical template with more than one fixated drill guide for multiple dental implant osteotomies.
Figure 14:
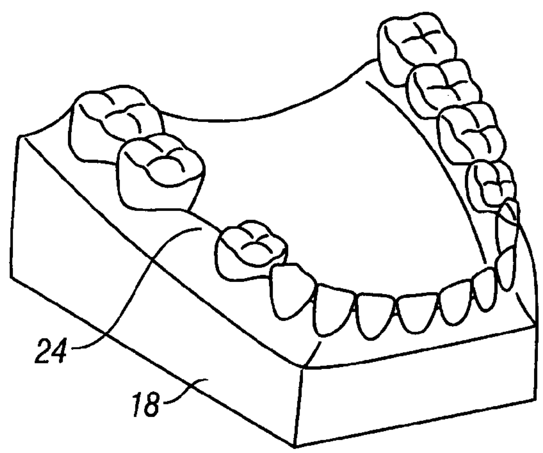
FIG. 14 shows a cast model of a patient's mandibular (lower) jawbone with an edentulous area.

FIGS. 12 and 13—Template and Top View

An alternative embodiment is a surgical template having more than one rigid drill guide 12 fixed in base 10, as shown in FIGS. 12 and 13. The number and position of drill guides 12 can vary to accommodate the different locations of missing teeth in a patient's dental arch. Base 10 can also have a different shape and dimension to accommodate the various arch sizes of the patient. Length 12B and inner diameter 12A of drill guides 12 can also vary to accommodate the many drill lengths and sizes of different dental implant systems in the market. However, the template remains a simple one-piece device with a secure locking mechanism 16 between drill guides 12 and base 10, enabling the surgeon to use it to perform multiple dental implant osteotomies.

FIGS. 14–17—Operation

A single dental implant osteotomy is performed as follows: First a cast model 18 (FIG. 14) of a patient's mandible or maxilla jawbone having an edentulous space 24 is prepared for evaluation. Next, a pre-molded surgical template (FIG. 1) with the appropriate size and shape is chosen for securing drill guide 12 used in performing the osteotomy.

Figure 15:
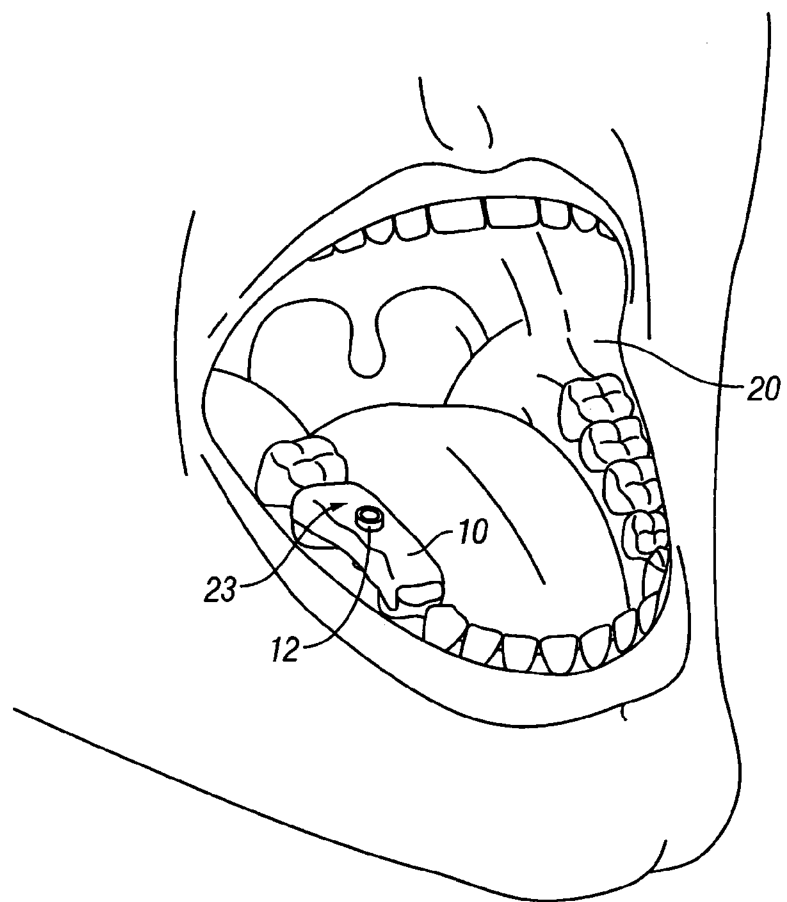
FIG. 15 shows a template molded and conformed directly in a patient's mouth to the teeth next to an edentulous area.
Figure 16:
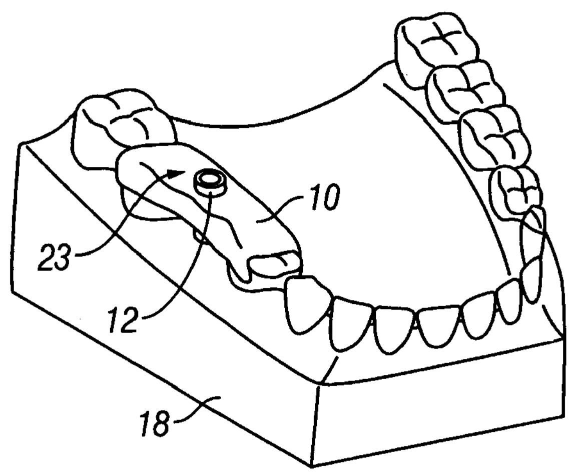
FIG. 16 shows a template molded and conformed on a cast model to the teeth next to an edentulous area.

The operator uses hot water to soften bas 10 until it just turns soft and malleable. Once base 10 is softened, the operator may then mold base 10 manually to conform to the surfaces of the teeth adjacent to the edentulous ridge. Base 10 is a substantially flat member having two opposing parallel sides and can be molded directly in the patient's mouth 20, as shown in FIG. 15; the material of base 10 will become soft and moldable at a temperature at which it can be manually molded by the dentist in mouth 20. Alternatively base 10 can be softened and manually molded on a cast model 18, as shown in FIG. 16. No additional tools are needed to mold base 10.

Before base 10 reaches room temperature and becomes rigid, drill guide 12 is adjusted to a desired position and axis corresponding to a prospective osteotomy. Typically, it should be halfway between the adjacent teeth at the correct angle in all directions to minimize the chance of post-surgical complications (such as nerve injury or sinus floor perforation). A skilled dental surgeon will be able to determine the appropriate positioning of drill guide 12.

In some cases where the template is molded indirectly on cast model 18, as shown on FIG. 16, the operator may elect to use a guide post that is secured in the model to facilitate adjusting the angle of drill guide 12.

Once base 10 cools to room temperature, it hardens with drill guide 12 firmly fixed in it. The resulting custom-molded template 23 (FIG. 15) is then removed from patient's mouth 20 or cast model 18 to check for retention and stability. Template 23 may be reheated and remolded a number of times to achieve the best custom fit. After the best fit is achieved, template 23 is then cold sterilized in an appropriate disinfectant. This whole process should take less than five minutes in the hands of a skilled user, thus saving a significant amount of time over fabricating a cured or vacuum-formed resin surgical template.

Figure 17:
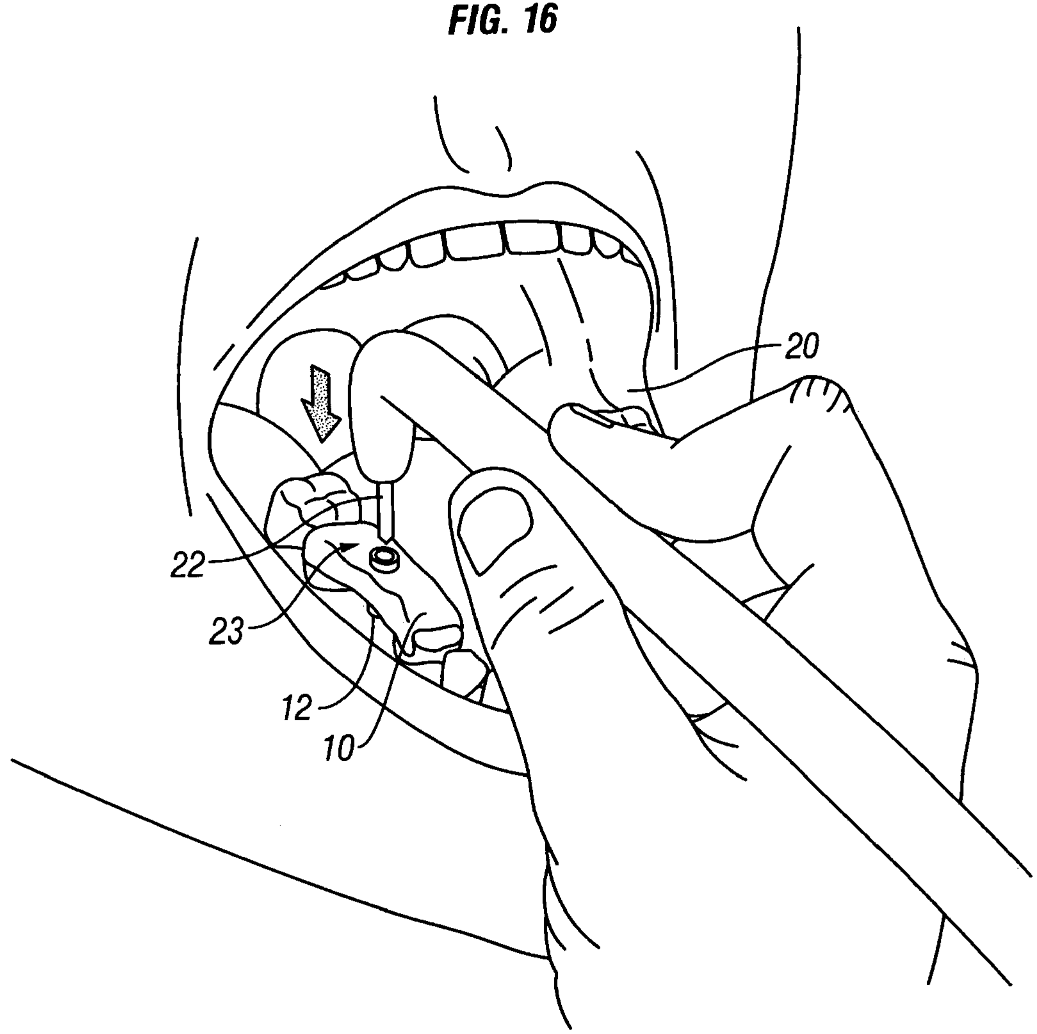
FIG. 17 shows a template molded and conformed directly in a patient's mouth to the teeth next to an edentulous area illustrating how the surgical template is used to guide the surgical drill during implant surgery.

Referring now to FIG. 17, template 23 is placed in the patient's mouth 20. If drill guide 12 is made of a radiopaque material such as stainless steel, a pre-operative radiograph (periapical, panoramic, etc.) is taken to verify that drill guide 12 is indeed angled in the right direction. Drill guide 12 also serves as a radiographic marker for evaluating vertical height of bone and tissue, as well as magnification rate of the radiograph, thus eliminating the need to fabricate a separate radiographic template. The patient's jawbone with the edentulous area 24 is then exposed by incision and retraction of soft tissue. Template 23 is then placed back into the patient's mouth 20. A surgical drill 22 is then used to prepare the bone to the desired depth using template 23 as a guide.

In some cases where successively larger drill bits are used to enlarge the osteotomy, the operator may elect to insert guide sleeves with smaller inner diameters than the drill guide diameter into template 23 to guide initially smaller drills. If necessary, further guide sleeves with increasing diameter may be used to gradually enlarge the osteotomy, therein successively larger drill bits are used. An implant is then inserted into the prepared site and after adding a cover screw or healing cap to the implant head the soft tissues are stabilized for healing. The custom-molded template 23 is then disposed of in an appropriate receptacle.

FIGS. 18–21—Operation for Multiple Osteotomies

Figure 18:
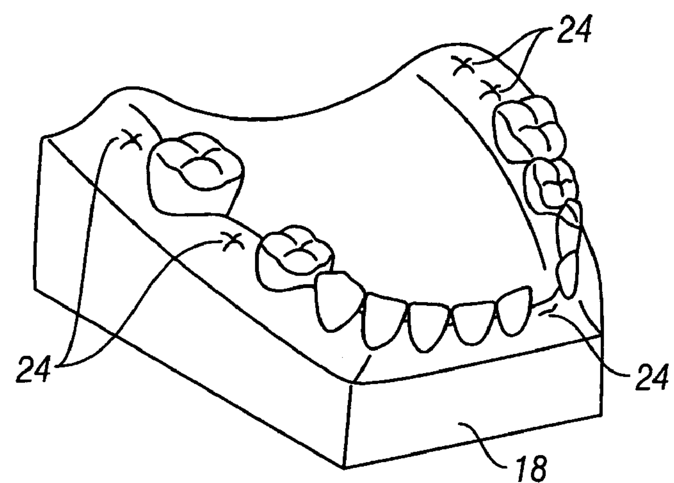
FIG. 18 shows a cast model of a patient's mandibular (lower) jawbone with more than one edentulous space.
Figure 19:
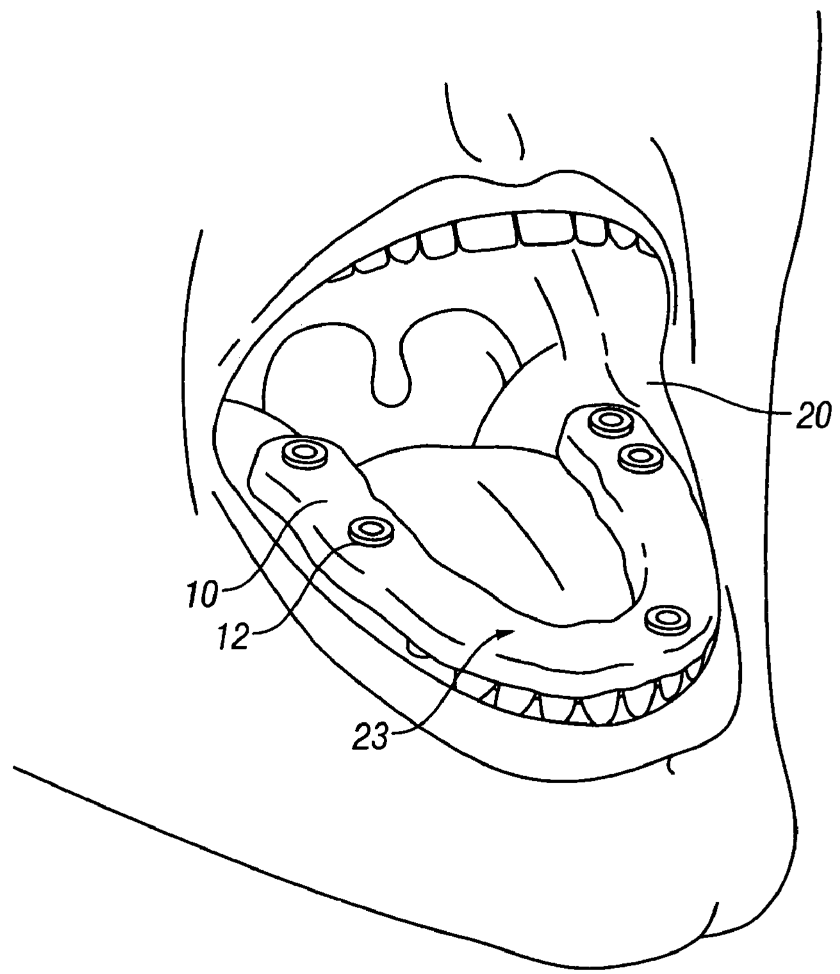
FIG. 19 shows a template with more than one fixated drill guide molded and conformed directly in a patient's mouth to the teeth next to an edentulous area.
Figure 20:
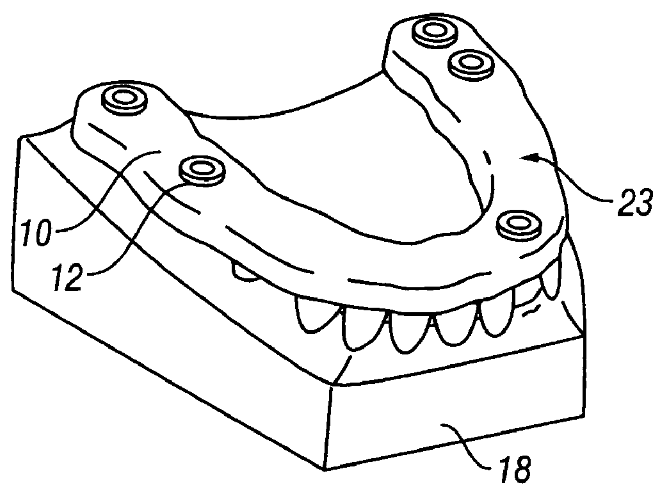
FIG. 20 shows a template with more than one fixated drill guide molded and conformed on a cast model to the teeth next to an edentulous area.
Figure 21:
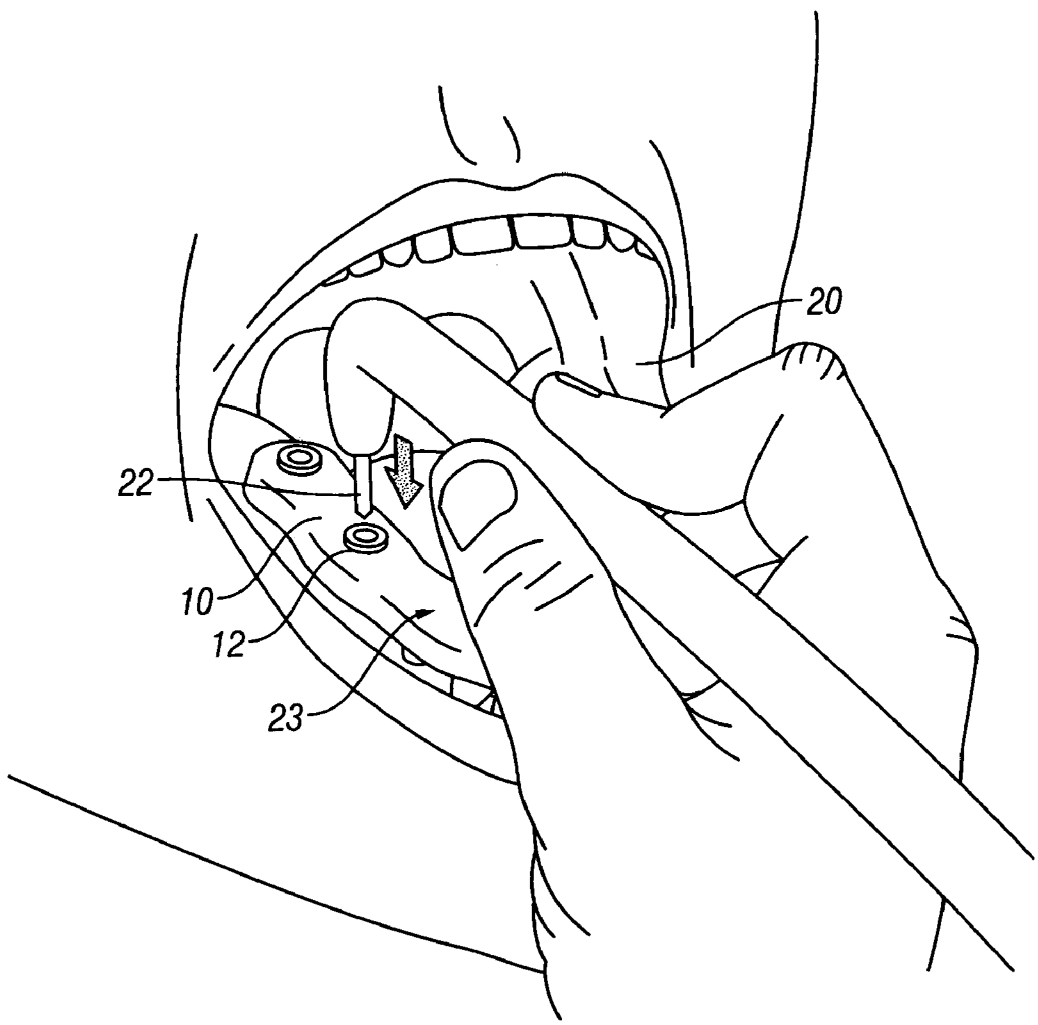
FIG. 21 shows a template with more than one fixated drill guide molded and conformed directly in a patient's mouth to the teeth next to an edentulous area illustrating how the surgical template is used to guide the surgical drill during implant surgery.

Another embodiment includes a method for performing multiple dental implant osteotomies. The steps for performing a single dental implant osteotomy may be adapted for performing multiple dental implant osteotomies as shown in FIGS. 19–21, where the patient has more than one edentulous space 24, as shown in FIG. 18, except that the template has more than one drill guide 12 fixed in base 10. Once base 10 is softened, the operator may mold base 10 manually to conform to the surfaces of the teeth adjacent to edentulous ridge 24, either directly in patient's mouth 20, as shown in FIG. 19 or on a cast model 18, as shown in FIG. 20. FIG. 21 shows custom-molded template 23 placed in mouth 20 with a surgical drill 22 being used to prepare the multiple osteotomies.

Figure 22:
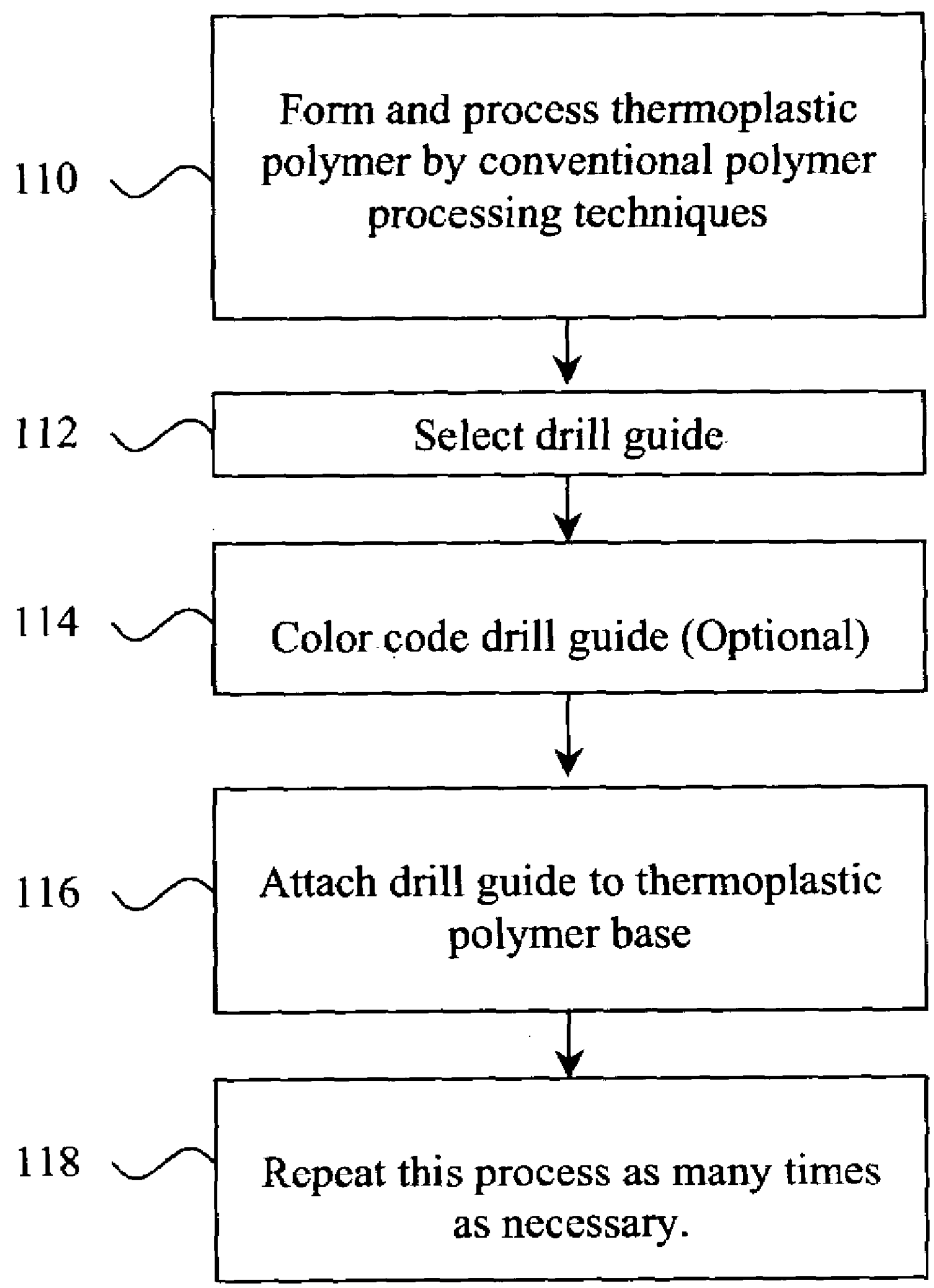
FIG. 22 shows a flow diagram illustrating a conventional method for manufacturing a surgical template.

FIG. 22—Manufacturing Flowchart

FIG. 22 is a flow diagram that illustrates a method for manufacturing the template. In step 110, a thermoplastic polymer is formed and processed by conventional polymer processing techniques into the desired shape to form base 10 of the template. Then a drill guide of appropriate length 12B and inner diameter 12A is selected, step 112. An optional step 114 of color coding drill guide 12 can be performed, using a pad print machine. The different colors correspond to the various inner diameters 12A. Drill guide 12 is then attached to thermoplastic polymer base 10, step 116. The process is repeated as many times as necessary, step 118. An exemplary method of conventional polymer processing is the extrusion technique. Heated polymer is forced through a die or jig in the form of the desired shape of base 10. The resulting shaped polymer emerges as a long sheet of the desired shape of base 10 which is then cooled and cut to produce individual base 10 pieces.

Figure 23:
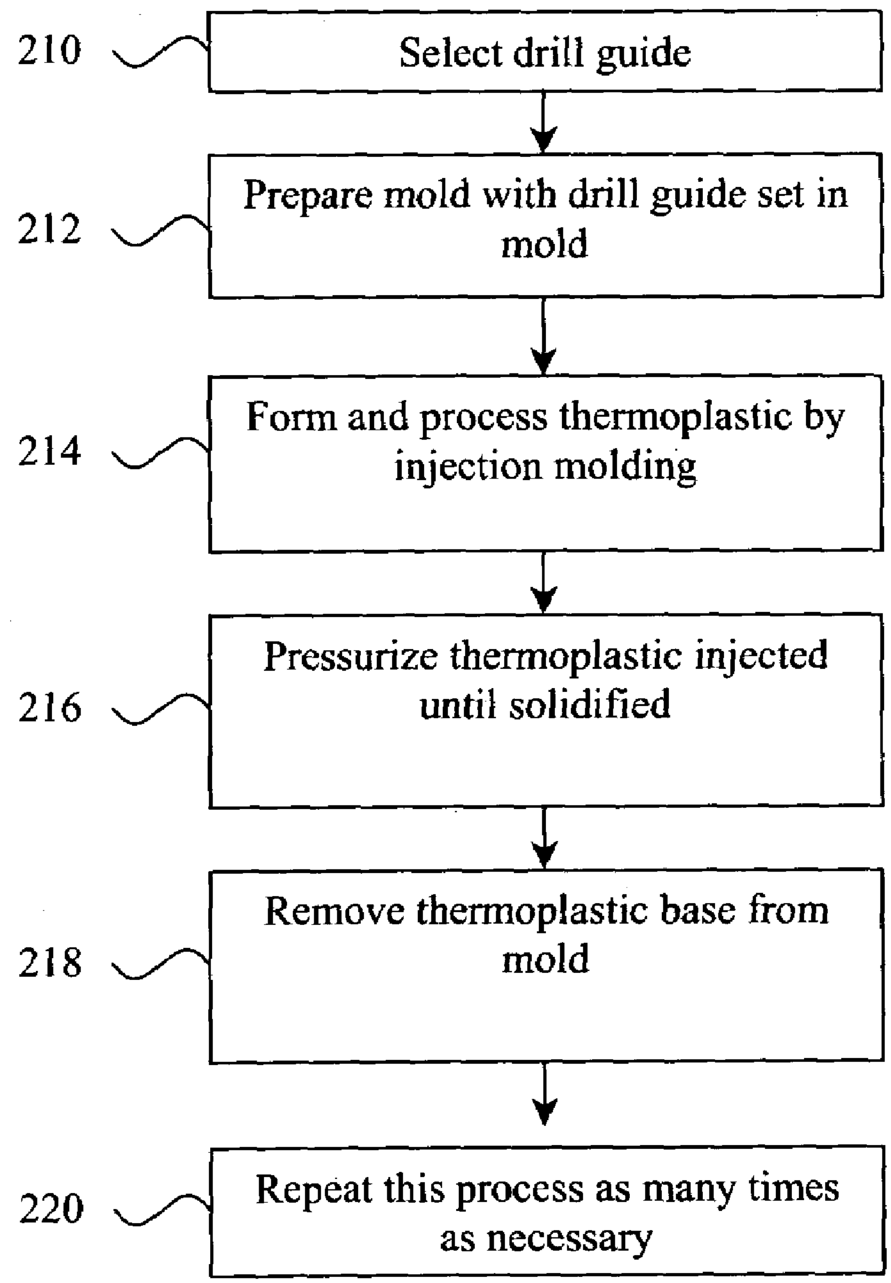
FIG. 23 shows a flow diagram illustrating a method for manufacturing a surgical template, preferably using injection molding.

FIGS. 22–23—Flow Chart—Alternative Method

FIG. 23 is a flow diagram that illustrates an alternative method for manufacturing the template, preferably using injection molding, according to another embodiment. The method preferably begins with a step 210 of selecting a drill guide 12 of appropriate length 12B and inner diameter 12A. Next, a mold is prepared with drill guide 12 set in the mold, step 212. The thermoplastic material is formed and processed, preferably by injection molding, step 214. The thermoplastic material is a thermoplastic polymer, such as TONE P-787 polymer. The thermoplastic injected is pressurized until it has solidified, step 216. The pressure is released and base 10 is removed from the mold, step 218. The process is repeated as many times as necessary, step 220.

The methods for manufacturing a template as shown in FIGS. 22 and 23 may be adapted to the preparation of the template having more than one rigid drill guide 12 fixed in base 10. A template having more than one drill guide 12 fixed in base 10 is manufactured from the same material and in the same manner as one having one rigid drill guide 12 fixed in base 10. The principal difference between the two is the additional drill guide insets in the molds for the template having more than one drill guide 12 fixed in base 10.

Conclusion, Ramifications, and Scope

Accordingly, the surgical template of the present invention provides a highly reliable, accurate, yet simple device that can be used by anyone skilled in the art of dental surgery. The template does not require complicated equipment, tools, steps, extraneous components and requirement, or advanced computer technology to fabricate. The operator needs only hot water to soften the base of the template so they can manipulate this device by hand alone, either directly in the patient's mouth or on a cast model to produce a custom-fit surgical template in minutes. Significant time and cost savings can therefore be realized by using this template to perform dental implant osteotomies.

While the description above contains many specificities, these should not be construed as limitations on the scope of the invention but as merely providing illustrations of some of the presently preferred embodiments of this invention. As discussed, many variations are possible. For example, the thermoplastic base can vary in size, shape, color, and composition; the drill guide can be color-coded and can vary in inner diameter and length; the locking mechanism between the base and the drill guide can vary; and the number and position of the drill guide fixed in the base can also vary. In addition, the operator can elect to use a guide post in the cast model to adjust the drill guide angulations, or to use a guide sleeve insert with reduced inner diameter to guide the initial smaller drill bit.

Thus the scope of the present invention should not be limited to the specific examples of the foregoing description, but rather is indicated by the appended claims and their legal equivalents.

I claim:

1. A method for performing a dental implant osteotomy using a template comprising a resinous, thermoplastic base; at least one non-thermoplastic, rigid drill guide attached to said base; and a securing mechanism between said base and said drill guide; comprising:

a. heat-softening said base until said base is malleable;
b. manipulating said base while malleable to conform to the teeth next to an edentulous ridge;
c. adjusting said drill guide to a desired position and axis corresponding to a prospective osteotomy;
d. allowing said template to cool until hardened;
e. verifying said template is stable in a patient's mouth and said drill guide is angled correctly in all directions;
f. drilling patient's bone with a drill bit using said template as a stable surgical guide;

whereby said method provides a one-piece device for performing dental implant osteotomies that can be easily fabricated by hand either directly in said patient's mouth or on a cast model.

2. The method according to claim 1 wherein said base material is arranged to reversibly melt to a malleable state upon heating in hot water between temperature range of 40–100° C., and remains moldable to conform to surfaces of teeth adjacent to said edentulous ridge before reaching room temperature.

3. The method according to claim 1 wherein said base is shaped and sized to match a predetermined arch size of a patient and to provide visual access to a surgical site during surgery.

4. The method according to claim 1 wherein said drill guide is fixed in said base and has a length and diameter selected to accommodate a predetermined drill size for a dental implant system.

5. The method according to claim 1 wherein said drill guide comprises a non-thermoplastic and rigid material selected from the group consisting of metals, ceramics, plastics, and composites.

6. The method according to claim 5 wherein said drill guide comprises a radiopaque material and said step of verifying angle of said drill guide further comprises taking x-rays to evaluate positioning, height of bone, and magnification rate prior to performing said osteotomy.

7. The method according to claim 1 wherein said drill guides are attached at a plurality of positions in said base corresponding to respective locations of a plurality of missing teeth where dental implant osteotomies are intended.

8. The method according to claim 1 wherein said securing mechanism is selected from the group consisting of bolt-and-nut, fastener, screw, click lock, and insert molding.

9. The method according to claim 1 wherein said template is repeatedly made malleable and hard for re-adjusting said drill guide to a desired position and axis corresponding to a prospective osteotomy.

10. The method according to claim 9 wherein said adjusting step further comprises using a guide post secured in a cast model to facilitate adjusting an angle of said drill guide while said base is malleable.

11. The method of claim 1, further comprising inserting a guide sleeve into said drill guide, said sleeve having a smaller inner diameter than said drill guide, wherein said sleeve guides a drill bit having a smaller diameter than that of said drill guide.

12. The method of claim 11 wherein one or more successively larger diameter guide sleeves are inserted into said drill guide for gradual enlargement of said osteotomy.

13. A device for guiding a dentist in performing a dental implant osteotomy on a patient, comprising:

a. a resinous, thermoplastic base formed of a material that is rigid at room temperature but that reversibly softens to a malleable state at a temperature that (a) is in the range of 40 to 100 degrees Celsius, and (b) allows said base to be placed in and molded in a patient's mouth; and
b. at least one non-thermoplastic, rigid drill guide attached to said base;

whereby said base, in its malleable state, may be conformed by hand to surfaces of the teeth adjacent to an edentulous ridge of said patient and said drill guide will be positioned for an intended osteotomy.

14. The device of claim 13 wherein said base is shaped and sized to accommodate a predetermined arch size of said patient and to allow visual access to a surgical site during surgery.

15. A kit comprising the device of claim 13 and a plurality of drill guides of various lengths and diameters for accommodating different drill sizes of different dental implant systems.

16. The kit of claim 15 wherein said drill guides are color-coded for different inner diameters to facilitate identification.

17. The kit of claim 15 wherein said drill guides attached at a plurality of positions in said base corresponding to locations of a plurality of missing teeth for a plurality of intended dental implant osteotomies.

18. The device of claim 13 wherein said drill guide comprises a non-thermoplastic and rigid material selected from a group consisting of metals, ceramics, plastics, and composites.

19. The device of claim 18 wherein said drill guide further comprises a radiopaque material for use as a marker for radiographic evaluation.

20. The device of claim 13, further including means for securing said drill guide to said base and preventing said base from detaching from said drill guide during surgery so as to provide a secure one-piece device.

21. The device of claim 13 wherein said base comprises a substantially flat member having two opposing parallel sides and said drill guide comprises a tubular member attached to said base and projecting from one said thereof.

22. The device of claim 13 wherein said base comprises a homopolymer of $\epsilon$-caprolactone.

23. A method of manufacturing a one-piece device for aiding a dentist in performing a dental implant osteotomy on a patient, comprising:

a. selecting at least one drill guide;
b. fabricating a base of a thermoplastic material;
c. said thermoplastic material of said base being rigid at room temperature but selected to reversibly soften to a malleable state at a temperature that (a) is the range of 40 to 100 degrees Celsius, and (b) allows said base to be placed in and molded in a patient's mouth, and
d. attaching said drill guide to said base;

whereby said base can be reversibly softened to a malleable state in hot water and then can be conformed by hand to surfaces of the teeth adjacent to an edentulous ridge so that said device remains as a one-piece device when said drill guide is positioned and said device is used for an intended osteotomy.

24. The method of claim 23 wherein said drill guide is color-coded.

25. The method of claim 23 wherein said base is fabricated by injection molding a thermoplastic polymer.

26. The method of claim 23 wherein said thermoplastic material is fabricated by extruding a thermoplastic polymer.

27. The method of claim 23 wherein attaching said drill guide to said base is done with a locking mechanism which prevents disassembly of said drill guide from said base.

28. The method of claim 27 wherein said locking mechanism is selected from the group consisting of bolt-and-nut, fastener, screw, click lock, and insert-molding locking mechanisms.

29. The method of claim 23 wherein said base comprises a substantially flat member having two opposing parallel sides and said drill guide comprises a tubular member attached to said base and projecting from one said thereof.

30. The method of claim 23 wherein said base is a homopolymer of ϵ-caprolactone.

31. A device for aiding a dentist in performing a dental implant osteotomy on a patient, comprising:

a. a resinous, thermoplastic base that is rigid at room temperature but that reversibly softens to a malleable state at temperature in the range of 40 to 100 degrees Celsius, b. said base being shaped and sized to accommodate a predetermined arch size of a patient and to allow visual access to a surgical site during surgery, c. at least one non-thermoplastic, rigid drill guide attached to said base; and d. means for securing said drill guide to said base;

whereby said base, in its malleable state, may be conformed by hand to surfaces of the teeth adjacent to an edentulous ridge of said patient and said drill guide will be positioned for an intended osteotomy.

32. The device of claim 31 wherein said base is formed of a material that reversibly melts to a malleable state upon heating in hot water in a temperature range of 40 to 100 degrees Celsius.

33. A kit comprising the device of claim 31 and a plurality of drill guides of various lengths and diameters for accommodating different drill sizes of different dental implant systems.

34. The kit of claim 33 wherein said drill guides are color-coded for different inner diameters to facilitate identification.

35. The kit of claim 33 wherein said drill guides are attached at a plurality of positions in said base corresponding to locations of a plurality of missing teeth for a plurality of intended dental implant osteotomies.

36. The device of claim 31 wherein said drill guide comprises a non-thermoplastic and rigid material selected from the group consisting of metals, ceramics, plastics, and composites.

37. The device of claim 36 wherein said drill guide further comprises a radiopaque material for use as a marker for radiographic evaluation.

38. The device of claim 31 wherein said means for securing said drill guide to said base is arranged to prevent said base from detaching from said drill guide during surgery so as to provide a secure, one-piece device.

39. The device of claim 31 wherein said base comprises a substantially flat member having two opposing parallel sides and said drill guide comprises a tubular member attached to said base and projecting from one said thereof.

40. The device of claim 39 wherein said base is a homopolymer of ϵ-caprolactone.

* * * * *